US00PP08132P

United States Patent [19]

Brooks, deceased et al.

[11] Patent Number: Plant 8,132

[45] Date of Patent: Feb. 9, 1993

[54] CHERRY TREE ROOTSTOCK 'BROOKS-60'

[75] Inventors: Lyle A. Brooks, deceased, late of Forest Grove, Oreg.; Wallace E. Heuser, legal representative, Hartford, Mich.

[73] Assignee: Inter-Plant Patent Marketing, Inc., Niagara-On-The-Lake, Canada

[21] Appl. No.: 768,119

[22] Filed: Sep. 30, 1991

Related U.S. Application Data

[63] Continuation of Ser. No. 371,676, Jun. 19, 1989, abandoned, which is a continuation of Ser. No. 162,670, Mar. 1, 1988, abandoned.

[51] Int. Cl.[5] ..... A01H 5/00

[52] U.S. Cl. ..... Plt./37

[58] Field of Search ..... Plt. 37

[56] References Cited

U.S. PATENT DOCUMENTS

| | | | |
|---|---|---|---|
| P.P. 5,159 | 12/1983 | Tydeman et al. | Plt. 37 |
| P.P. 5,801 | 11/1986 | Monin et al. | Plt. 37 |
| P.P. 5,802 | 11/1986 | Monin et al. | Plt. 37 |
| P.P. 5,803 | 11/1986 | Monin et al. | Plt. 37 |
| P.P. 6,676 | 3/1989 | Hansche | Plt. 37 |

*Primary Examiner*—Howard J. Locker
*Attorney, Agent, or Firm*—Dykema Gosset

[57] ABSTRACT

This is a new and distinct cherry tree, given the varietal name of "Brooks-60 cultivar", which will be marketed as "MXM-60." It is characterized by its exceptional resistance to Phytophthora and its precocity.

3 Drawing Sheets

This application is a continuation application of Ser. No. 07/371,676, filed on Jun. 19, 1989, now abandoned, which is a continuing application of Ser. No. 07/162,670, filed Mar. 1, 1988, now abandoned.

BACKGROUND OF THE INVENTION

This distinct new cherry cultivar was discovered during the Summer of 1958 by Lyle A. Brooks, whose resided at 2515 Gales Way, Forrest Grove, Oreg. 97116. It was selected from a population of approximately 30,000 open pollinated *Prunus mahaleb* seedlings growing in a nursery field near Fairview, Oreg. The seed used to grow these *Prunus mahaleb* seedlings came from a seed orchard that has *Prunus mahaleb* and *Prunus avium* fruiting trees growing side by side. During the Spring of 1957 a rare weather occurrence brought the bloom period of both these species together, resulting in a small portion of the seed population having *Prunus mahaleb* as the seed parent and *Prunus avium* as the pollen parent. During the Summer of 1958, the inventor, Lyle Brooks, selected 100 specimens exhibiting visual hybrid characteristics from the large 30,000 seedling population. Brooks then started a screening and evaluation process with the goal of producing an improved cherry rootstock. The rootstock screening process included comparison with various common scion varieties. Investigations were made respecting clonal rooting ability, disease resistance, hardiness and compatability, precocity, productivity and tree size. The Brooks-60 cultivar was found in a cultivated area near Fairview, Oreg., and was asexually reproduced by Lyle A. Brooks by softwood cuttings near Fairview, Oreg. The asexually reproduced plants firmly retain the unique combination of characteristics which are disclosed in the specification as defining the cultivar for which patent protection is sought.

SUMMARY OF THE INVENTION

Brooks-60 cultivar as a rootstock produces a tree that has been compatible with all scion varieties tested to date. The tree size is about 85% of *Prunus avium* and similar to *Prunus mahaleb*. It is well anchored and more precocious than either parent. It is very hardy and drought resistant. The cultivar has shown exceptional resistance to Phytophthora species and is more resistant to *Phytophthora cactorum* than either parent.

The upper surfaces of the leaves of the parent varieties, *Prunus mahaleb* and *Prunus avium* are substantially different than those of Brooks-60. The leaves of *Prunus mahaleb* are generally light green and those of *Prunus avium* are a dull, dark green.

Brooks-60 as a rootstock results in earlier production of fruit of the grafted plants than with the parent varieties and is healthier than either parent. Brooks-60 has substantially greater longevity than either *Prunus mahaleb* or *Prunus avium* and can survive in a greater range of climates and soil than the parent varieties, particularly in heavier, slow draining soils. Brooks-60 consistently comes into production earlier than Brooks-2.

THE DRAWINGS

DETAILED DESCRIPTION

Figure 1:
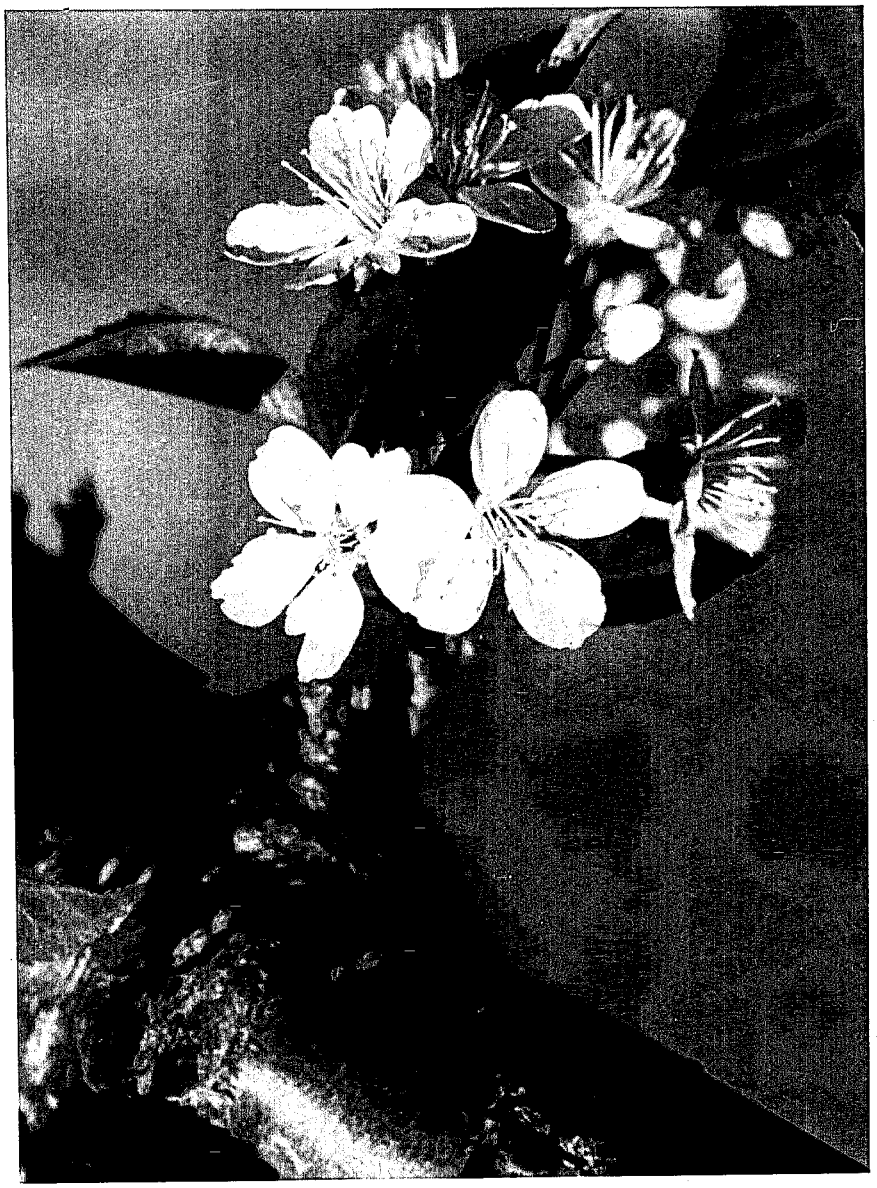
FIG. 1 is a color photograph which shows typical blooms and foliage of the new cultivar.
Figure 2:
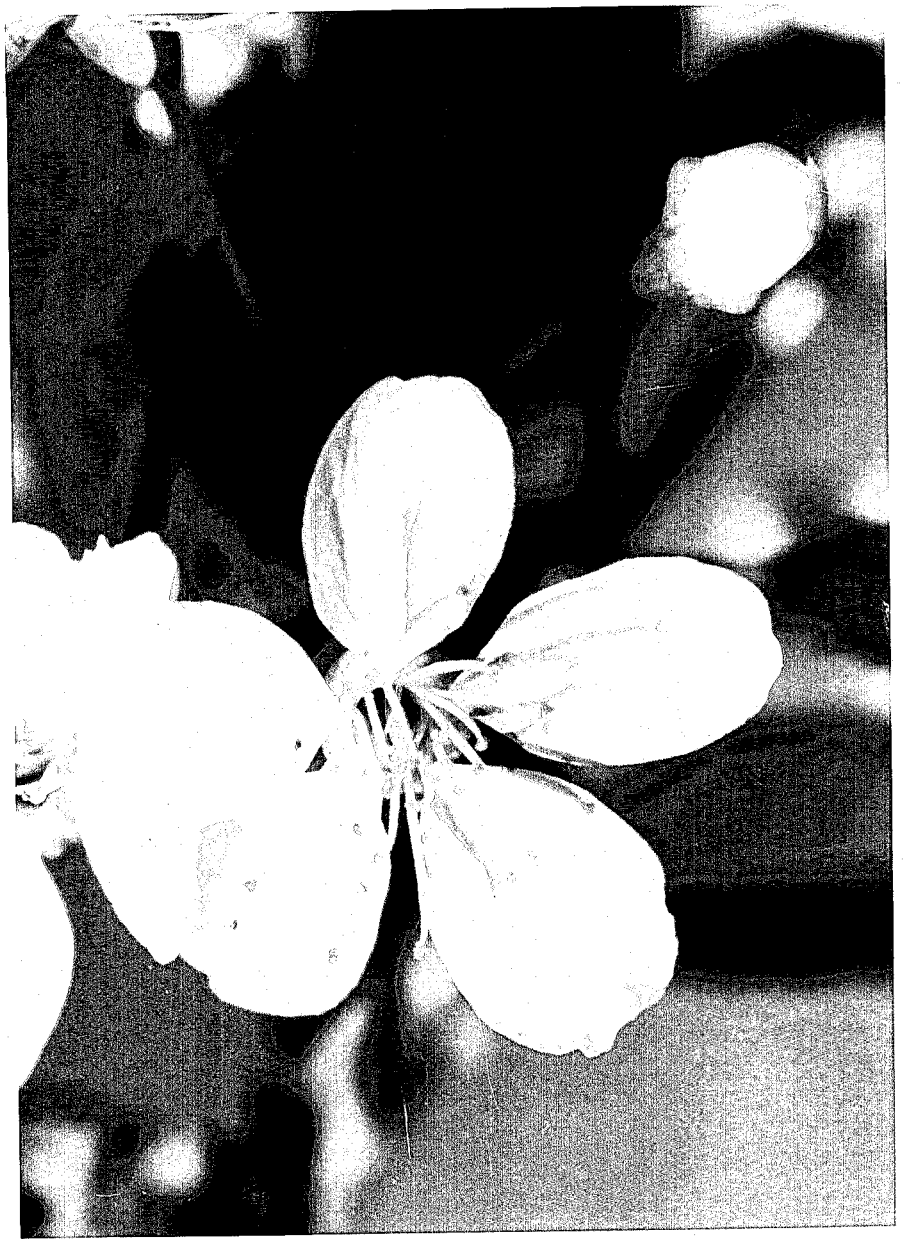
FIG. 2 is a color photograph depicting a close-up of the blossom.
Figure 3:
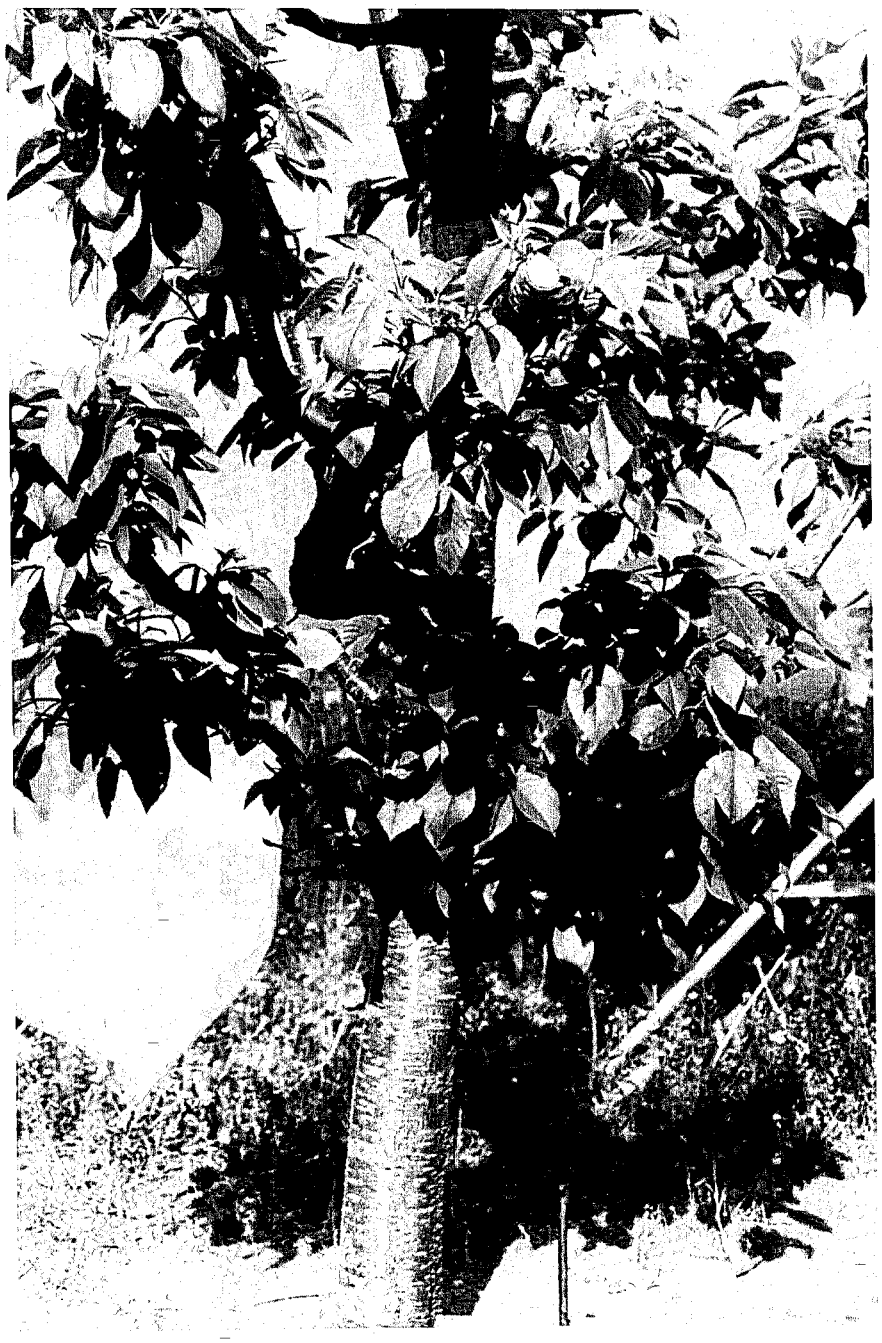
FIG. 3 is a color photograph which shows the entire plant.

This new cultivar serves as a support for other cherry trees grafted thereon. To Applicant's knowledge, the rootstock per se has not been fruited and thus, a description of the fruit is not available. Therefore, the fruit and seed produced on the rootstock depend upon the characteristics of the cherry tree cultivars which are grafted thereon.

Leaves:

*Size.*—Width 3.4 to 4.0 cm, Length 6.5 to 7.4 cm.

*Shape.*—Simple, ovate with rounded base and acuminate tips, margin serrate with some teeth tipped with small, dark glands. Brooks-60 leaves are generally rounder than those of Brooks-2.

*Surface.*—Upper surface glabrous, lower surface with fine, white pubescence along midriff and primary veins. Brooks-60 has a smoother, more waxy leaf than Brooks-2.

*Color.*—Non-glossy, olive green (R.H.S. plate 137A) on upper surface, light green (RHS plate 148B) lower surface.

Petiole:

*Color.*—Red-purple (R.H.S. plate 60A).

*Pubescence.*—Very fine, short, white, scattered hairs.

*Margin.*—Smooth.

*Shape.*—Narrow, slender, reddish brown.

*Glands.*—2 prominent, reniform glands at base of leaf blade.

*Length.*—1.5 to 1.9 cm.

Flower:

*Color.*—White.

*Shape.*—Simple, 5 petals, 25 anthers, 1 pistil.

*Petals.*—Round, 7 mm slightly pointed where attached.

*Stem.*—1.7 to 2 cm average length.

*Blossoms.*—5–6 blossoms per flower bud.

Buds:

*Length.*—0.2 to 0.4 cm, tight, medium brown, conical, 3/1 Phyllotaxy.

General growth habit: Vigorous, open and spreading, at maturity, erect and unbranched in nursery row. A ten year study has demonstrated that Brooks-60 has greater longevity than either parent variety. The trunk of a four year tree is on average approximately 42 $cm^2$ in cross-section, somewhat less than that of four year Brooks-2. After grafting, trees of the same age show a slight difference in height between Brooks-60 and Brooks-2 with Brooks-60 being slightly shorter.

Wood:

*Color.*—Light brown with slight reddish overcolor.

*Texture.*—Smooth to slightly ridged.

*Internodes.*—2.0 to 2.8 on current seasons growth.

*Lenticels.*—Very few, scattered, small, very slightly raised, lenticular, light tan colored.

*Tree size.*—(Of scion) Semi-standard, tree with maturity approximately 70–75% the size of same scion on *Prunus avium.*

Root system: Very fibrous, more so than either parent variety.

Fruit: The fruit of Brooks-60 has not been observed. It is believed that Brooks-60 is sterile.

I claim:

1. A cherry tree rootstock plant substantially as herein described and illustrated.

* * * * *

UNITED STATES PATENT AND TRADEMARK OFFICE

CERTIFICATE OF CORRECTION

PATENT NO. : PP08132

DATED : February 9, 1993

INVENTOR(S) : Brooks,

It is certified that error appears in the above-indentified patent and that said Letters Patent is hereby corrected as shown below:

On the title page, Item [75] Inventors: "Wallace E. Heuser, legal representative, Hartford, Mich." should be deleted.

Signed and Sealed this

First Day of March, 1994

*Attest:*

*Attesting Officer*

BRUCE LEHMAN

*Commissioner of Patents and Trademarks*